(12) United States Patent
Cho et al.

(10) Patent No.: US 10,458,901 B2
(45) Date of Patent: Oct. 29, 2019

(54) APPARATUS AND METHOD FOR SIMULTANEOUSLY MEASURING CHARACTERISTICS OF MOLECULAR JUNCTIONS AND REFRACTIVE INDEX OF BUFFER SOLUTION

(71) Applicant: Korea Research Institute of Standards and Science, Daejeon (KR)

(72) Inventors: Hyun Mo Cho, Daejeon (KR); Yong Jai Cho, Daejeon (KR); Won Chegal, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 454 days.

(21) Appl. No.: 14/432,066

(22) PCT Filed: Sep. 27, 2013

(86) PCT No.: PCT/KR2013/008656
§ 371 (c)(1),
(2) Date: Mar. 27, 2015

(87) PCT Pub. No.: WO2014/061924
PCT Pub. Date: Apr. 24, 2014

(65) Prior Publication Data
US 2015/0253243 A1    Sep. 10, 2015

(30) Foreign Application Priority Data

Oct. 15, 2012 (KR) .......................... 10-2012-0114097

(51) Int. Cl.
*G01N 21/21*    (2006.01)
*G01N 21/05*    (2006.01)
(Continued)

(52) U.S. Cl.
CPC .......... *G01N 21/211* (2013.01); *G01N 21/05* (2013.01); *G01N 21/41* (2013.01); *G01N 21/253* (2013.01);
(Continued)

(58) Field of Classification Search
CPC ............... G01N 21/554; G01N 21/211; G01N 2021/215
See application file for complete search history.

(56) References Cited

U.S. PATENT DOCUMENTS 4,508,832 A * 4/1985 Carter .................. G01N 21/211
                                                           356/246
4,999,014 A * 3/1991 Gold .................... G01N 21/211
                                                           356/369
(Continued)

FOREIGN PATENT DOCUMENTS

JP      2010019594 A    1/2010
KR   1020010107735      2/2008
(Continued)

OTHER PUBLICATIONS

Kriss, "Powerpoint Presentation", 2nd International Conference on Label-Free Technologies, Mar. 12-14, 2015, Boston, MA, 4 slides.
(Continued)

*Primary Examiner* — Tri T Ton
*Assistant Examiner* — Rufus L Phillips
(74) *Attorney, Agent, or Firm* — Kaplan Breyer Schwarz, LLP

(57) ABSTRACT

An apparatus and method for simultaneously measuring, in an immersion microchannel environment, the characteristics of molecular junctions such as a low-molecular-weight biomaterial and the like and the refractive index of a buffer solution by using ellipsometry. Specifically, disclosed is an apparatus for simultaneously measuring, with high sensitiv-
(Continued)

ity, the change in refractive index of a buffer solution and the junction dynamic characteristics of a biomaterial by allowing polarized incident light to be received at a biomaterial adsorption layer, which is formed on a substrate such as a semiconductor and the like, so as to meet an anti-reflection condition of a P-wave by using a prism structure and a microchannel; and a measurement method using the same.

18 Claims, 11 Drawing Sheets

(51) Int. Cl.
  *G01N 21/41* (2006.01)
  *G01N 21/25* (2006.01)
(52) U.S. Cl.
  CPC ............... *G01N 2201/0683* (2013.01); *G01N 2201/06113* (2013.01)

(56) References Cited

U.S. PATENT DOCUMENTS

| | | | | |
|---|---|---|---|---|
| 5,501,637 A * | 3/1996 | Duncan | ............... | G01J 5/0003 250/225 |
| 2004/0142482 A1* | 7/2004 | Westphal | ............. | G01N 21/211 436/164 |
| 2010/0259754 A1* | 10/2010 | Hooper | ............... | G01N 21/211 356/369 |
| 2012/0295357 A1* | 11/2012 | Cho | ............... | B01L 3/502715 436/34 |

FOREIGN PATENT DOCUMENTS

| | | | |
|---|---|---|---|
| KR | 20110056720 A | 5/2011 | |
| WO | WO 2011062377 A2 * | 5/2011 | ........ B01L 3/502715 |

OTHER PUBLICATIONS

Lecture Itinerary, Solution immersed cilicon (SIS)-based biosensors for acute myocardial infarction diagnosis, ICSE-7, Berlin, Jun. 6-10, 2016, 1 pp.

Cho et al., "Simultaneous measurements of the molecular interactions and refractive index of buffer solution using solution immersed silicon biosensor", 2nd International Conference on Label-Free Technologies, Mar. 12-14, 2015, Boston, MA, 1 pp.

Cho et al., "Solution immersed silicon (SIS)-based biosensors for acute myocardial infarction", ICSE-7, Berlin, Jun. 6-10, 2016, p. 101.

Diware et al., "Synchronous measurement of thickness and refractive index by SIS sensors: and effective way of biosensing", Elsevier, Feb. 1, 2017, pp. 1-7.

Diware et al., "Ultrasensitive, Label-free detection of cardiac biomarkers with optical SIS sensor", Supporting Information, Center for Nanometrology, Department of Mechanical System Engineering, Department of Bio-Microsystem Technology, 3 pp.

Diware et al., "Untrasensitive, label-free detection of cardiac biomarkers with optical SIS Sensor", Elsevier Publication, Biosensors and Bioelectronics, 2017, vol. 87, pp. 242-248.

"International Application No. PCT/KR2013/008656", "International Search Report", dated Jan. 6, 2014, Publisher: International Searching Authority / KR, Published in: KR.

* cited by examiner

Fig. 3
(PRIOR ART)
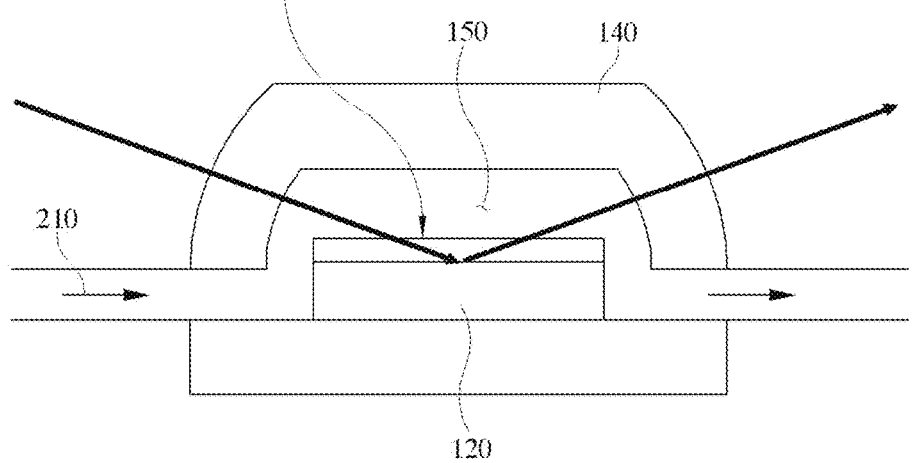
Wavelength of light source : 655 nm
Refractive index of buffer solution medium : n = 1.333, n = 1.334
Bio-thin film adsorption layer + Self-assembled monolayer : 4 nm, 5 nm, n = 1.45
Refractive index of substrate material : n = 3.8391, k = 0.018186
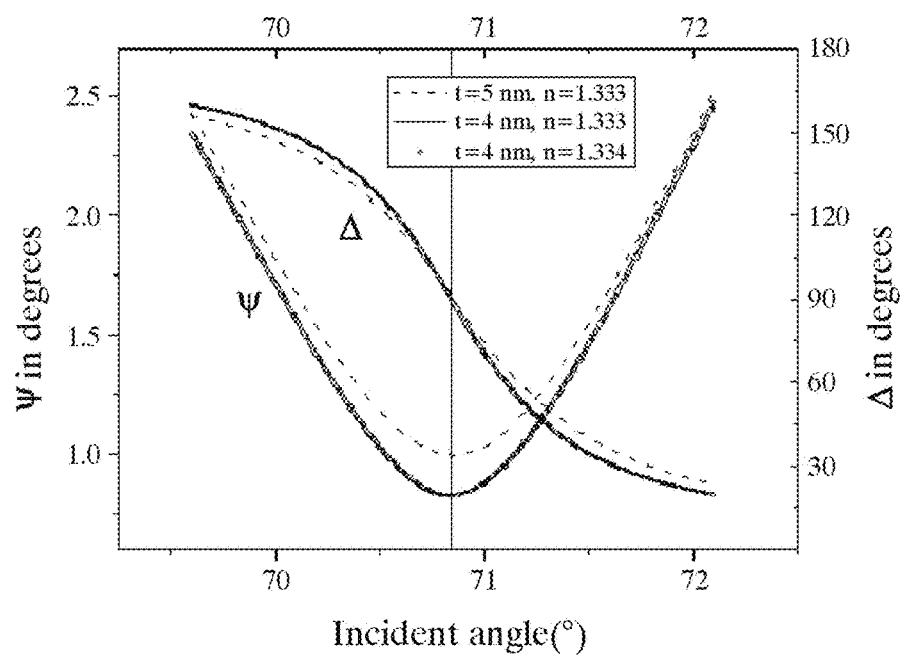

Fig. 11
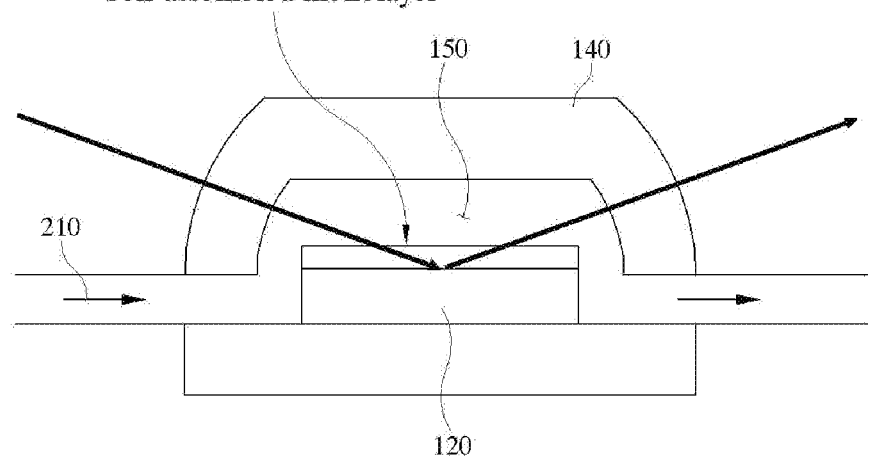
Wavelength of light source : 655 nm
Refractive index of buffer solution medium : n=1.333, n=1.3332
Bio-thin film adsorption layer + Self-assembled monolayer : 4 nm, n=1.45
Refractive index of substrate material : n=3.8391, k=0.018186
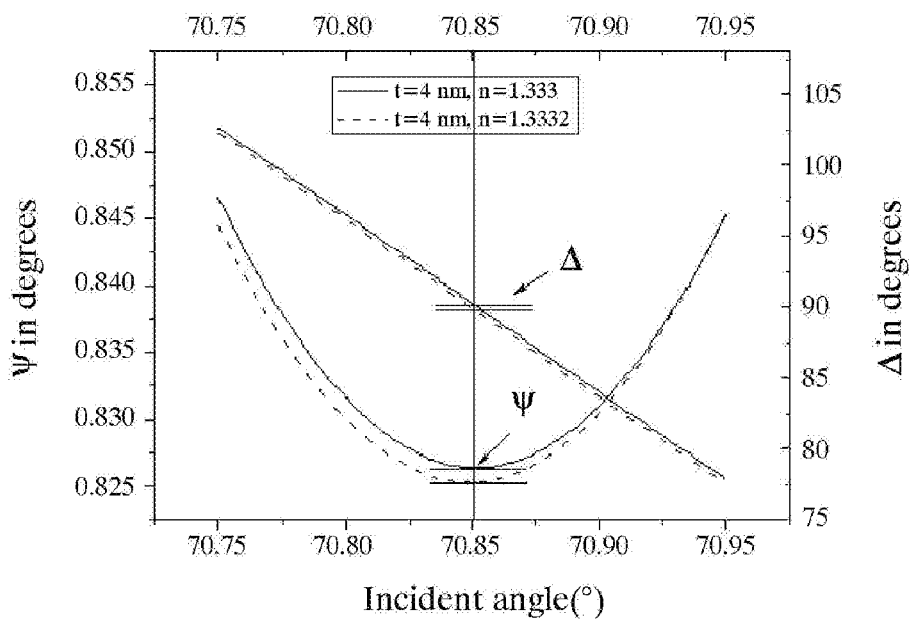

Wavelength of light source :655 nm
Refractive index of buffer solution medium :n=1.333, n=1.3332
Bio-thin film adsorption layer + Self-assembled monolayer :4 nm, n=1.45
Refractive index of substrate material :n=3.8391, k=0.018186

APPARATUS AND METHOD FOR SIMULTANEOUSLY MEASURING CHARACTERISTICS OF MOLECULAR JUNCTIONS AND REFRACTIVE INDEX OF BUFFER SOLUTION

FIELD OF THE INVENTION

The present invention relates to an apparatus and a method for simultaneously measuring, in an immersion microchannel environment, the characteristics of molecular junctions of a material such as a low-molecular-weight biomaterial and the refractive index of a buffer solution by using ellipsometry. More specifically, the present invention relates to an apparatus for simultaneously measuring with high sensitivity a change in the refractive index of a buffer solution and the junction kinetics of a biomaterial by allowing polarized incident light to be received on a biomaterial adsorption layer, which is formed on a substrate such as a semiconductor and the like, so as to meet a P-wave anti-reflection condition by using a prism structure and a microchannel; and a measurement method using the same.

BACKGROUND OF THE INVENTION

Reflectometry and ellipsometry are light analysis techniques that measure a change in reflective index or polarization of light reflected from a surface of a sample and analyze the measured value to determine a thickness or optical property of the sample.

A reflectometer and an ellipsometer are meters using these techniques. They are used to assess a thickness of various thin films at nano-scale and properties thereof in a nano-thin film manufacturing process of semiconductor industry. Furthermore, the use of them has been expanded to bio-industries and efforts are made to apply to interfacial analysis of biomaterials such as proteins, DNAs, viruses, new drug materials, and the like.

A conventional reflectometer is sufficient to assess a thickness and property of a nano-thin film having a size more than few nanometers (nm), but it has a problem of low reliability due to low detection sensitivity in analysis of a low molecular weight biomaterial which needs sensitivity in the range of about 10.001 nanometers. An ellipsometer has detection sensitivity not more than 0.01 nm compared to the reflectometer, and particularly it has high detection sensitivity under a condition with a large reflective index difference such as measuring a thickness of an oxide film having relatively smaller reflective index compared to a semiconductor onto a semiconductor substrate having a high reflective index.

However, a measurement method having enhanced sensitivity is needed to analyze a low molecular weight biomaterial using the ellipsometer.

As a conventional technique for enhancing detection sensitivity in analysis of biomaterials, there is a surface plasmon resonance sensor (hereinafter, it is referred to as 'SPR sensor') in which the reflectometry is mixed with surface plasmon resonance (SPR).

The surface plasmon resonance (SPR) is that electrons present on a metal surface are excited by light waves to cause collective vibration in a normal direction of the surface and absorb light energy. It has been known that the SPR sensor can measure a thickness of a nano-thin film adjacent to the metal surface and a change in reflective index using surface plasmon resonance phenomenon sensitive to polarization of light, as well as allow real-time measurement on a change in adsorption concentration of biomaterials in a non-labeling manner without a fluorescent material.

The SPR sensor is made of a material such as glass coated with a metal thin film in few tens of nanometers, onto which the sensor is attached; the sensor may be bonded with a biomaterial. When a sample in a buffer solution is bonded with the sensor, a resonance angle is changed. The resonance angle is determined by measuring a reflective index. When light enters the SPR sensor, the glass material serves as an incident medium. The light passes through the thin film bonded with the biomaterial, and ultimately the buffer solution serves as a substrate.

In such a configuration, a bio-thin film layer shows a change upon binding with a measured sample, and a shift in resonance angle is directly affected by a refractive index of a buffer solution acting as a substrate. Therefore, to measure pure junction kinetics, the refractive index of the buffer solution should be independently measured and corrected.

To correct a change in reflective index of the buffer solution and avoid an error due to diffusion between the buffer solution and the sample, a method such as using a delicate valve device, an air injection device, and two or more channels and using one channel as a reference channel for correction has been proposed. However, it is difficult to distinguish a SPR angle shift by the reflective index change of the buffer solution from a SPR angle shift by pure adsorption and dissociation property, which may act as a factor causing an error in measurement. Consequently, the conventional SPR sensor shows substantially a difficulty in measuring adsorption and dissociation property of low molecular weight materials due to the foregoing limitation.

Furthermore, the conventional SPR sensor employs a metal thin film made of a noble metal such as gold (Au), silver (Ag) and the like, thereby increasing production costs. Such a metal thin film has uneven roughness according to manufacturing processes and exhibits a large deviation in refractive index. Also, it is difficult to quantitatively measure biomaterials due to unstable optical property. In addition, the SPR sensor comprises an error due to different sensitivities at different positions in relatively comparing with a reference channel.

To improve the foregoing disadvantages of the SPR sensor, a biomaterial binding sensor layer is formed onto the substrate such as silicon, and an amplitude and a phase of light reflected from the substrate through the buffer solution is measured at the P-wave antireflection condition under an immersion microchannel environment using ellipsometry. In this way, a signal of which the measured amplitude is not sensitive to the refractive index change of the buffer solution, but is sensitive to the junction kinetics of the biomaterial can be obtained. Contrary to the SPR measurement, when the junction property of the biomaterial adsorbed on the substrate is measured under an immersion microchannel environment, the buffer solution serves as an incident medium, and light passing through the biomaterial adsorption layer is reflected from the substrate.

In this measurement condition, a measured ellipsometric angle is not sensitive to the refractive index change of the buffer solution serving as an incident medium, but is sensitive to a change of the bio-thin film and the substrate. When a substrate material such as silicon having a stable refractive index is used, since a signal that a measured ellipsometric angle is only sensitive to a change of the bio-thin film can be obtained, the foregoing problems of the SPR method can be solved. However, this method may be applied only when the refractive index change of the buffer solution is negligibly smaller than an ellipsometric angle shift by binding with the bio-thin film. If the refractive index change of the buffer solution is significantly larger than the ellipsometric angle shift by binding with the bio-thin film, the refractive index change should be measured and corrected.

When a solvent having a high refractive index is used for dissolving a sample in a buffer solution or an additional solution is added in the buffer solution to improve surface junction characteristics, one needs a new method for simultaneously and independently measuring the refractive index of the buffer solution and the biomaterial junction characteristics to correct the refractive index of the buffer solution FIG. 1 shows a configuration of the prior patent wherein a sensor layer is formed onto a substrate such as silicon and measurement is performed under an immersion microchannel environment using ellipsometry to improve the foregoing disadvantages of the SPR sensor. As shown in FIG. 1, the sensor for measuring biomaterial junction characteristics according to the prior patent comprises roughly a microchannel structure unit (100), a substrate (120), a cover part (140), a microchannel (150), a sample injection part (200), a polarized light-generating part (300) and a polarized light-detecting part (400). The sensor for measuring biomaterial junction characteristics according to the prior patent has an adsorption layer (160) formed onto the substrate (120) or a dielectric thin film (130), and forms an immersion environment of the microchannel (150). When a buffer solution (210) containing a biomaterial sample (1) dissolved therein is injected into the microchannel (150), the biomaterial is adsorbed on a ligand material (2) formed on a surface of the adsorption layer (160) to form an adsorption layer having a desired thickness.

Then, polarized incident light from the polarized light-generating part (300) enters a boundary surface between the buffer solution (210) and the substrate (120) through an incident surface (142) at an angle of a P-wave anti-reflection condition. Light reflected from the substrate (120) contains optical data on the adsorption layer of the sample (1). That is, the molecular adsorption and dissociation kinetics such as an adsorption concentration, a thickness of the adsorption layer or a refractive index are changed during the adsorption and dissociation process of the sample (1) to the ligand (2), and hence a measured ellipsometric angle are shifted. The reflected light containing optical data is detected in the polarized light-detecting part (400) through the buffer solution (210) and a reflective surface (144). The polarized light-detecting part (400) measures a change in polarized components of the reflected light, thereby determining the molecular adsorption and dissociation kinetics of the sample (1).

FIG. 2 shows an adsorption curve illustrating an adsorption process of a sample (32) to a metal thin film (20) and a dissociation curve illustrating a dissociation process. A larger adsorption rate constant (ka) means faster absorption of a biomaterial, and a smaller dissociation rate constant (kd) means slower dissociation.

In other words, a dissociation constant (KD=kd/ka) in equilibrium can be calculated by determining the adsorption rate constant and the dissociation rate constant. For example, it can be determined whether a low molecular weight material such as a new drug candidate for a cancer inhibitor may be practically used as a new drug by measuring adsorption or dissociation property of the material to a protein containing a cancer inducer.

Hereinafter, the features and the limitations of the sensor for analyzing biomaterials according to the prior patent will be described with reference to FIG. 3 and FIG. 4. FIG. 3 shows a graph of ellipsometric constants $\Psi$ and $\Delta$ on light entering the immersion microchannel structure at the perpendicular in the sensor according to the prior patent. As in FIG. 1, a silicon substrate and a light source (40) having 655 nm wavelength were used.

4 nm and 5 nm thicknesses of a bio-thin film adsorption layer including a thickness of a self-assembled monolayer were respectively measured. The adsorption layer having the refractive index (n) of 1.45 was measured, and buffer solutions having the refractive index (n) of 1.333 and 1.334 were measured. As shown in FIG. 3, a change of $\Psi$ due to the thin film thickness change is relatively larger than a change of $\Psi$ due to the refractive index change. Thus, it can be seen that most $\Psi$ values are caused by the thickness variation.

This largely solves problems caused by a large refractive index change due to a buffer solution in the conventional SPR method, but does not simultaneously measure and correct the refractive index of the buffer solution. This method has an advantage that pure junction kinetics can be measured when a biomaterial sample on which the junction characteristics are measured do not exhibit a large change in refractive index in dissolving it in the buffer solution.

However, if there is a sample which is not well dissolved in the buffer solution, a solvent having a large refractive index difference such as dimethyl sulfoxide (DMSO) may be used, or other materials having different refractive indexes may be added in the buffer solution to increase an electrostatic binding ability and control a pH value. Where a large change in refractive index exhibits by mixing other solvents or materials having different refractive indexes with the pure buffer solution, the refractive index of the buffer solution should be simultaneously measured and corrected. In case that the buffer solution exhibits such large refractive index change, since a change due to the thin film thickness and the refractive index of the buffer solution are together contained in a measured signal, a signal shift by the buffer solution is not negligible.

It can be seen from FIG. 3 that the change of $\Psi$ by perpendicular incident light is directly sensitive to the biomaterial junction kinetics, but the change of $\Delta$ is little changed by the thickness or the refractive index change of the buffer solution at an angle which meets the P-wave anti-reflection condition.

FIG. 4 is a schematic view illustrating a problem of the conventional technique that inherent adsorption kinetics of a sample during an adsorption and dissociation process of the sample is mixed with the refractive index change of a buffer solution. FIG. 4(a) is a graph of an inherent adsorption and dissociation concentration of the sample (32). FIG. 4(b) is a graph illustrating a change in measured result depending on the refractive index change of the buffer solution (34). FIG. 4(c) is a graph of an adsorption and dissociation concentration of the sample (32) measured from the sensor when the inherent adsorption kinetics of the sample (32) is mixed with the refractive index change of the buffer solution. That is, a signal of the sensor is sensitive to an effect of the refractive index change of the buffer solution (34) (arrow), but the adsorption and dissociation concentration of only the sample (32) is unclear. Accordingly, there is a problem that it is difficult to analyze this result and calculate the adsorption and dissociation concentration of the sample (32).

This problem is caused when the refractive index change of the buffer solution during injecting the sample is relatively larger than the signal shift in the sensor by the biomaterial junction characteristics. In particular, this problem is caused when a solvent having a large refractive index difference from the buffer solution is used in mixing the sample with the buffer solution, or other materials used for increasing binding effectiveness has a large refractive index difference from the buffer solution. The conventional SPR sensor shows the foregoing problem even when the refractive index change is minor during injecting the sample. Further, even if substantially the same solutions are injected, the SPR signal shift is significantly larger than the biomaterial junction characteristics, acting as a fundamental factor causing a measurement error.

To correct the refractive index change of the buffer solution (34) and avoid an error due to diffusion between the sample (32) and the buffer solution (34), a method such as using a delicate valve device, an air injection device, and two or more channels and using one channel as a reference channel for correction has been proposed. However, it is different to distinguish the refractive index change of the buffer solution from a change by pure adsorption and dissociation property, and it may always act as a factor causing a measurement error. Consequently, due to said limitations of measurement using the conventional sensor, when the refractive index change of the buffer solution is relatively larger during injecting the sample, there is a fundamental difficulty in measuring dissociation property.

Furthermore, the conventional method can correct a signal varying with time and space only when the reference channel and other channels have constant sensor sensitivity, and a minor change in sensitivity may act as a measurement error factor. In particular, in the SPR sensor, a metal thin film such as gold (Au), silver (Ag) and the like has high production costs, a large deviation in refractive index according to manufacturing processes compared to a semiconductor substrate such as silicon, and unstable optical property. Accordingly, the SPR sensor has a problem that an error is caused due to different sensitivities at different positions in relatively comparing with a reference channel.

SUMMARY OF THE INVENTION

Technical Task

The present invention is to solve the foregoing problems. It is an object of the present invention to provide an apparatus and a method for simultaneously measuring the characteristics of molecular junctions and the refractive index of a buffer solution that can measure only pure junction kinetics excluding an effect of the refractive index of the buffer solution by simultaneously measuring a change in the refractive index of the buffer solution and the junction kinetics of a biomaterial under an immersion microchannel environment when a signal shift of a sensor due to the refractive index change of the buffer solution is relatively larger than a signal shift due to the junction kinetics of the biomaterial upon injecting a sample, and that can measure the junction kinetics of the biomaterial with high sensitivity by counteracting the refractive index change of the buffer solution and hence an incident angle change when a signal shift of a sensor due to the refractive index change of the buffer solution is relatively larger than a signal shift due to the junction kinetics of the biomaterial upon injecting a sample.

It is another object of the present invention to provide an apparatus and a method for simultaneously measuring the characteristics of molecular junctions and the refractive index of a buffer solution that can enhance reliability and effectiveness in a study of molecular junction kinetics by using an optimized microchannel structure and a valve device to enable simultaneous measurement of the refractive index change of a buffer solution and the junction kinetics of a biomaterial for high sensitive analysis of the biomaterial.

Other objectives, certain advantages and new features of the present invention will be more apparent from the following description and preferred examples with reference to the accompanying drawings.

Means for Achieving the Task

A first object of the present invention can be achieved by an apparatus for simultaneously measuring the characteristics of molecular junctions and the refractive index of a buffer solution comprising a microchannel structure unit provided with a substrate made of a support and a semiconductor or a dielectric material formed on the support, a cover part of a prism structure fitted on the support and a microchannel formed in either of a top of the support or a bottom of the cover part; a sample injection part for injecting a buffer solution containing a biomaterial sample into the microchannel to form an adsorption layer of the sample on the substrate; a polarized light-generating part for irradiating incident light polarized through an incident surface of the prism on the adsorption layer at an incident angle of a P-wave anti-reflection condition; and a polarized light-detecting part for detecting a change in polarization of reflected light.

An additional dielectric thin film may be used between the substrate and the adsorption layer onto the substrate. The dielectric thin film is made from a transparent semiconductor oxide film or a glass film, and a thickness thereof is greater than 0~1000 nm.

A second object of the present invention can be achieved by an apparatus for simultaneously measuring the characteristics of molecular junctions and the refractive index of a buffer solution comprising a microchannel structure unit provided with a substrate made of a support and a semiconductor or a dielectric material formed on the support, a dielectric thin film provided onto the substrate, a cover part of a prism structure fitted on the support and a microchannel formed in either of a top of the support or a bottom of the cover part; a sample injection part for injecting a buffer solution containing a biomaterial sample into the microchannel to form an adsorption layer of the sample on the dielectric thin film; a polarized light-generating part for irradiating incident light polarized through an incident surface of the prism on the adsorption layer at an incident angle of a P-wave anti-reflection condition; and a polarized light-detecting part for detecting a change in polarization of reflected light when the reflected light enters a reflective surface of the prism from the adsorption layer.

The adsorption layer is a multilayer film consisting of a self-assembled monolayer for junction characteristics of various biomaterials, an immobilization substance and a biomaterial including low molecular weight materials bonded with the immobilization substance.

The polarized light-generating part comprises a light source configured to irradiate a desired light and a polarizer configured to polarize the irradiated light.

The light source may irradiate monochromatic light or white light.

The light source may be a laser or a laser diode.

Further, the light source may be a laser or a laser diode which has a variable form of wavelength.

The polarized light-generating part comprises at least one of a collimating lens to provide parallel lights to the polarizer; a focusing lens to converge the parallel lights passing through the polarizer to increase the quantity of incident light; and a first compensator to cause phase lag in polarized components of the incident light.

The polarizer and the first compensator may be rotatable, or may have an additional polarization-modulating means.

A third object of the present invention can be achieved by a microchannel structure unit used for an apparatus for simultaneously measuring the characteristics of molecular junctions and the refractive index of a buffer solution wherein the microchannel structure unit comprises a support; a substrate made of a semiconductor or a dielectric material and formed on one side of the support; a cover part of a prism structure fitted on the support; and a microchannel formed in either of a top of the support or a bottom of the cover part; wherein the buffer solution containing a biomaterial sample is injected into the microchannel to form an adsorption layer on the substrate, incident light polarized through an incident surface of the prism is irradiated on the adsorption layer at an incident angle of a P-wave anti-reflection condition, and light reflected from the adsorption layer is emitted through a reflective surface of the prism.

When the prism structure is a prism, an incident surface of the prism allows light to be received at an approximately perpendicular angle. Also, a light-emitting surface, which forms a boundary surface with the buffer solution, allows light to be received on a substrate at an inclined angle which can meet the P-wave anti-reflection condition, not light entering at the perpendicular to the buffer solution. A top surface of the prism structure may be shaved in a trapezoidal shape, or may have a free shape. It is important that light is received on the boundary surface at an inclined angle. A flat plate may be also used instead of the prism structure.

A fourth object of the present invention can be achieved by a microchannel structure unit used for an apparatus for simultaneously measuring the characteristics of molecular junctions and the refractive index of a buffer solution wherein the microchannel structure unit comprises a support; a substrate made of a semiconductor or a dielectric material and formed on one side of the support; a dielectric thin film provided onto the substrate; a cover part of a prism structure fitted on the support; and a microchannel formed in either of a top of the support or a bottom of the cover part; wherein the buffer solution containing a biomaterial sample is injected into the microchannel to form an adsorption layer on the dielectric thin film onto the substrate, incident light polarized through an incident surface of the prism is irradiated on the adsorption layer at an incident angle of a P-wave anti-reflection condition, and light reflected from the adsorption layer is emitted through a reflective surface of the prism.

The microchannel has a plurality of inflow passages formed in one side of the support and a plurality of outflow passages formed in the other side. The inflow passages and the outflow passages are respectively connected through a plurality of septums formed in the bottom of the prism.

The microchannel may be formed as a single channel type microchannel, and a plurality of different self-assembled monolayers may be provided on the dielectric thin film to adsorb the sample.

A fifth object of the present invention can be achieved by a system for simultaneously analyzing the characteristics of molecular junctions and the refractive index of a buffer solution comprising a microchannel structure unit provided with a substrate made of a support and a semiconductor or a dielectric material formed on the support, a cover part of a prism structure fitted on the support and a microchannel formed in either of a top of the support or a bottom of the cover part; a sample injection part for injecting a buffer solution containing a biomaterial sample into the microchannel to form an adsorption layer of the sample on the substrate; a polarized light-generating part for irradiating incident light polarized through an incident surface of the prism on the adsorption layer at an incident angle of a P-wave anti-reflection condition; a polarized light-detecting part for detecting a change in polarization of reflected light when the reflected light enters a reflective surface of the prism from the adsorption layer; and an analyzing means electrically connected to the polarized light-detecting part for analyzing the refractive index of the buffer solution and the characteristics of molecular junctions of the sample based on the polarization change.

The polarized light-detecting part comprises an analyzer configured to polarize reflected light and a light detector which detects the polarized reflected light to obtain optical data.

The light detector may be any one of a CCD type solid state imaging element, a photomultiplier tube and a silicon photodiode.

The analyzing means comprises a processor which is electrically connected to the light detector to calculate values based on the optical data. The processor calculates an ellipsometric constant on a phase difference in ellipsometry to determine the refractive index of the buffer solution, and calculates an ellipsometric constant on an amplitude ratio to determine values including an adsorption concentration of the sample, an adsorption and dissociation constant of the sample, and the like.

The polarized light-detecting part may further comprise at least one of a second compensator to cause phase lag in polarized components of reflected light and a spectrometer to resolve reflected light.

The analyzer and the second compensator may be rotatable, or may have an additional polarization-modulating means.

A sixth object of the present invention can be achieved by a method for simultaneously measuring the characteristics of molecular junctions and the refractive index of a buffer solution comprising the first step (S100) of injecting a buffer solution containing a low molecular weight biomaterial sample into the microchannel of the microchannel structure unit by the sample injection part; the second step (S200) of forming an adsorption layer by adsorbing the sample on the substrate of the microchannel structure unit; the third step (S300) of polarizing a desired light by the polarized light-generating part and receiving the light on the adsorption layer at an incident angle which meets the P-wave anti-reflection condition through the incident surface of the prism of the microchannel structure unit; the fourth step (S400) of polarizing a desired light by the polarized light-generating part and receiving light reflected from the adsorption layer on the polarized light-detecting part at an incident angle which meets the P-wave anti-reflection condition through an incident window of the microchannel structure unit; and the fifth step (S500) of detecting the polarization of the reflected light by the polarized light-detecting part using ellipsometry or reflectometry.

The fifth step (S500) comprises the steps of polarizing the reflected light by the analyzer, detecting the polarized reflected light by the light detector to obtain a desired optical data, and calculating an ellipsometric constant on a phase difference in ellipsometry by the analyzing means based on the optical data to determine the refractive index of the buffer solution, and calculating an ellipsometric constant on an amplitude ratio to determine values including an adsorption concentration of the sample, an adsorption and dissociation constant of the sample, and the like.

Effect of the Invention

As described above, the apparatus and the method for simultaneously measuring the characteristics of molecular junctions and the refractive index of a buffer solution according to the present invention employ the substrate made of a semiconductor or a dielectric material in which the prism structure and the microchannel are coupled for adsorbing a sample, instead of using a metal thin film, and simultaneously measure the junction characteristics and the refractive index of the buffer solution, thereby accurately determining inherent adsorption and dissociation kinetics of only the sample. Further, the present invention, by using the substrate made of a cheap semiconductor or a dielectric material, has an advantage that production costs are largely reduced.

Furthermore, the present invention allows high sensitivity measurement in that the present invention utilizes ellipsometry and reflectometry under a P-wave anti-reflection condition and provides a high quantity of incident light using a laser, a laser diode, or the like, in order to increase a signal to noise ratio. Moreover, the present invention, by using the prism incident mechanism, has an advantage that it can measure the junction characteristics at an amplitude ratio ($\Psi$) with high sensitivity under a P-wave anti-reflection condition upon ellipsometry, and simultaneously measure a phase difference ($\Delta$) with high sensitivity to detect only an effect of the pure refractive index of the buffer solution.

Further, the microchannel structure unit of the present invention is provided with the microchannel coupled to the prism optimized for analysis of biomaterials. The microchannel comprises multi-channels or a single channel onto which a plurality of self-assembled monolayers are formed. Accordingly, the present invention has an advantage that various experimental conditions may be provided such as injecting various concentrations of a sample into the multi-channels of the microchannel or varying an adsorption degree of the self-assembled monolayer, thereby increasing effectiveness of biomaterial analysis.

Further, the present invention allows high sensitivity measurement of biomaterials under an immersion microchannel environment in a non-labeling manner and may be used in various industries such as bio, medicine, food, environment and the like.

Although the present invention has been described with respect to the foregoing preferred examples, one with ordinary skill in the art will appreciate that various modifications and variations are made without departing from the spirit and the scope of the present invention. Also, it is obvious that such modifications and variations fall within the scope of the attached claims.

BRIEF DESCRIPTION OF THE DRAWINGS

FIG. 3 is a graph illustrating ellipsometric constants $\Psi$ and $\Delta$ according to adsorption of a biomaterial and the refractive index change of a buffer solution measured by using the sensor for measuring the junction characteristics of a biomaterial known in the prior patent.

FIG. 11 is a graph illustrating ellipsometric constants $\Psi$ and $\Delta$ according to the refractive index change of a buffer solution measured by using the sensor for measuring the junction characteristics of a biomaterial known in the prior patent, which measures at the perpendicular incident condition.

DESCRIPTION OF REFERENCE NUMBERS

Figure 1:
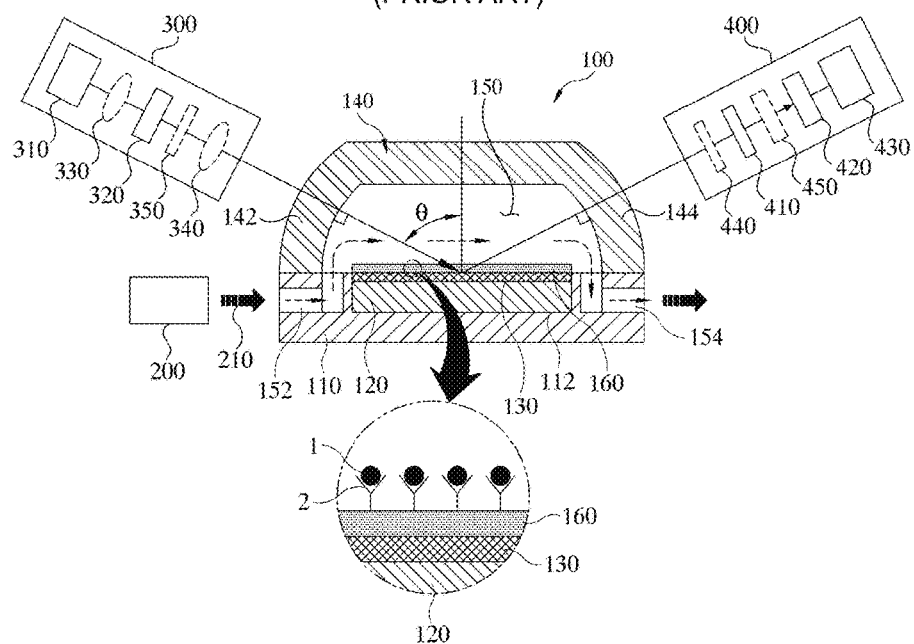
FIG. 1 is a cross-sectional view showing a sensor for measuring the junction characteristics of a biomaterial known in the prior patent.
Figure 2:
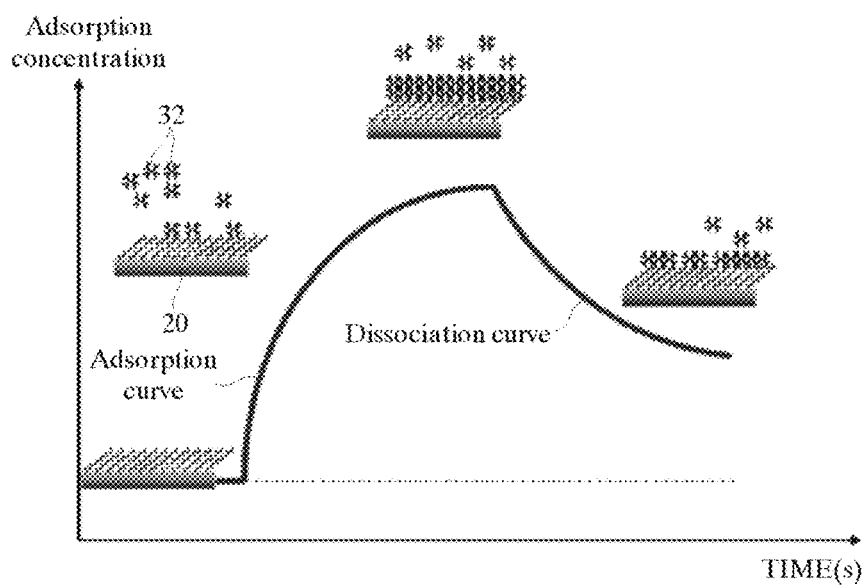
FIG. 2 is a schematic view showing a change in adsorption concentration in an adsorption and dissociation process of a sample onto a metal thin film.
Figure 4:
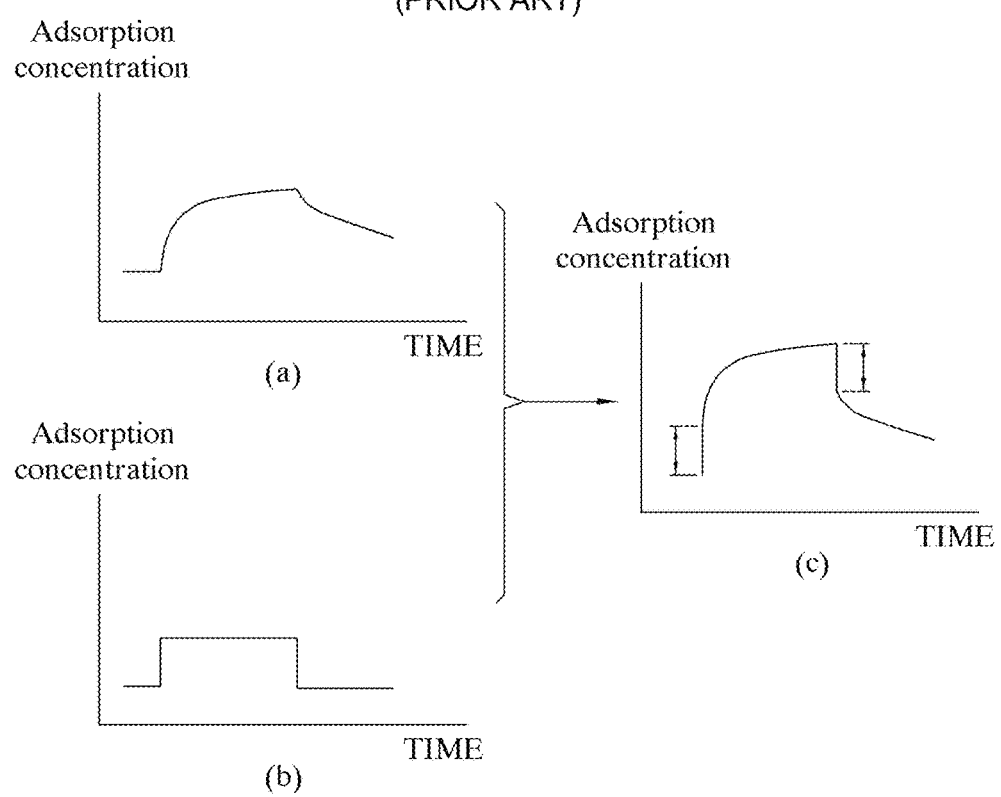
FIG. 4 is a schematic view illustrating a problem of the conventional technique that inherent adsorption and dissociation kinetics of a sample in an adsorption and dissociation process of the sample is mixed with the refractive index change of a buffer solution.

100: microchannel structure unit 110: support
112: recess portion 120: substrate
130: dielectric thin film 132: self-assembled single layer film
140: cover part 142: prism
143: incident surface 144: reflective surface
146: septum 150: microchannel
152: inflow passage 154: outflow passage
160: adsorption layer 200: sample injection part
210: buffer solution 300: polarized light-generating part
310: light source 320: polarizer
330: collimating lens 340: focusing lens
350: first compensator 400: polarized light-detecting part
410: analyzer 420: light detector
430: processor 440: second compensator
450: spectrometer

DETAILED DESCRIPTION

Hereinafter, preferred examples will be described in detail with reference to the accompanying drawings in order for one with ordinary skill in the art to easily practise the present invention. A specific description on a known relevant function or constitution may be omitted in describing an operation mechanism with respect to the preferred examples not to makes the present invention obscure.

Throughout the drawings, the same reference numbers are allocated to parts having similar functions. Also, throughout the specification, when a part is connected to other parts, it comprises a direct connection as well as an indirect connection with other elements therebetween. Furthermore, by comprising a component means that other components may further included but excluding other components unless otherwise indicated.

[Configuration of an Apparatus for Simultaneously Measuring the Characteristics of Molecular Junctions and the Refractive Index of a Buffer Solution]

Firstly, a configuration of the apparatus for simultaneously measuring the characteristics of molecular junctions and the refractive index of a buffer solution according to an example of the present invention will be described with reference to the accompanying drawings.

Figure 5:
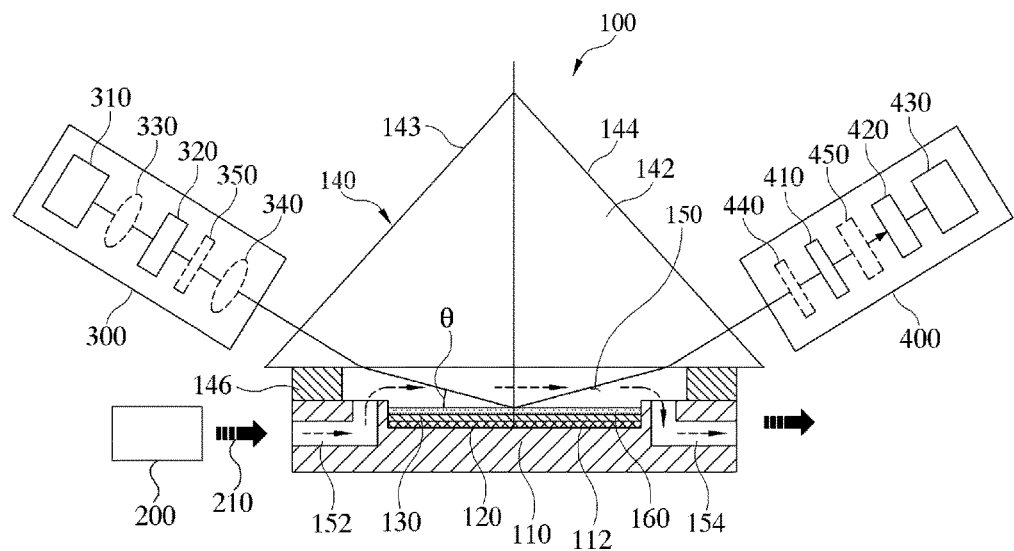
FIG. 5 is a cross-sectional view showing a configuration of the apparatus for simultaneously measuring the characteristics of molecular junctions and the refractive index of a buffer solution according to an example of the present invention.

FIG. 5 is a schematic view showing a configuration of the apparatus for simultaneously measuring the characteristics of molecular junctions and the refractive index of a buffer solution according to an example of the present invention. As shown in FIG. 5, the apparatus for simultaneously measuring the characteristics of molecular junctions and the refractive index of a buffer solution according to an example of the present invention comprises roughly a microchannel structure unit (100) which provides an immersion microchannel environment and an optical system which comprises a polarized light-generating part (300) providing a sample injection part (200) and incident light and a polarized light-detecting part (400) detecting a change in polarization of reflected light.

The present invention is to measure the adsorption and dissociation kinetics of a biomaterial including low molecular weight materials using ellipsometry, in which a buffer solution (buffer) (210) containing a sample of the biomaterial (not shown) is injected from the sample injection part (200) to the microchannel structure unit (100). The microchannel structure unit (100) has a microchannel (150) which may be a multi-channel or single-channel type, as will be described below.

Figure 6:
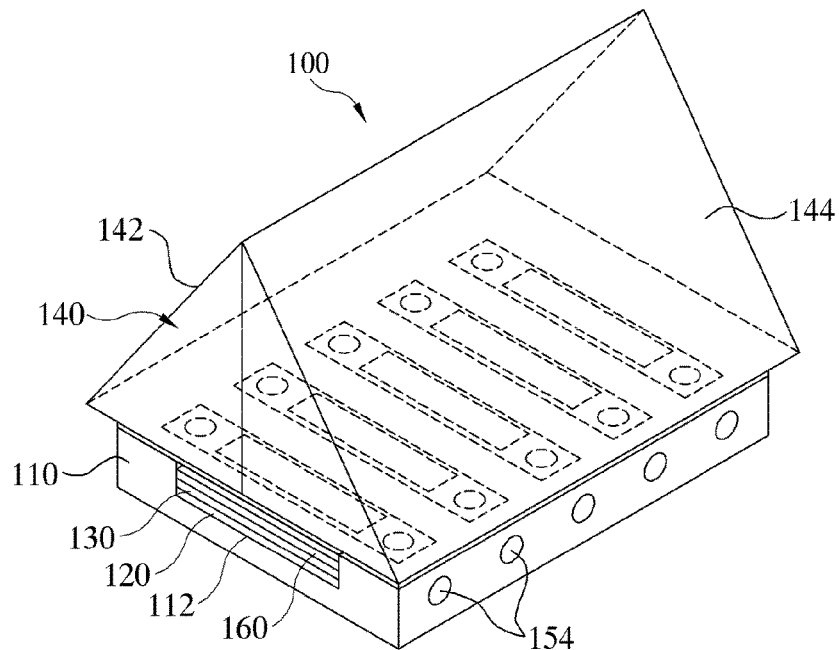
FIG. 6 is a perspective view of a multi-channel type microchannel structure unit according to an example of the present invention.
Figure 7:
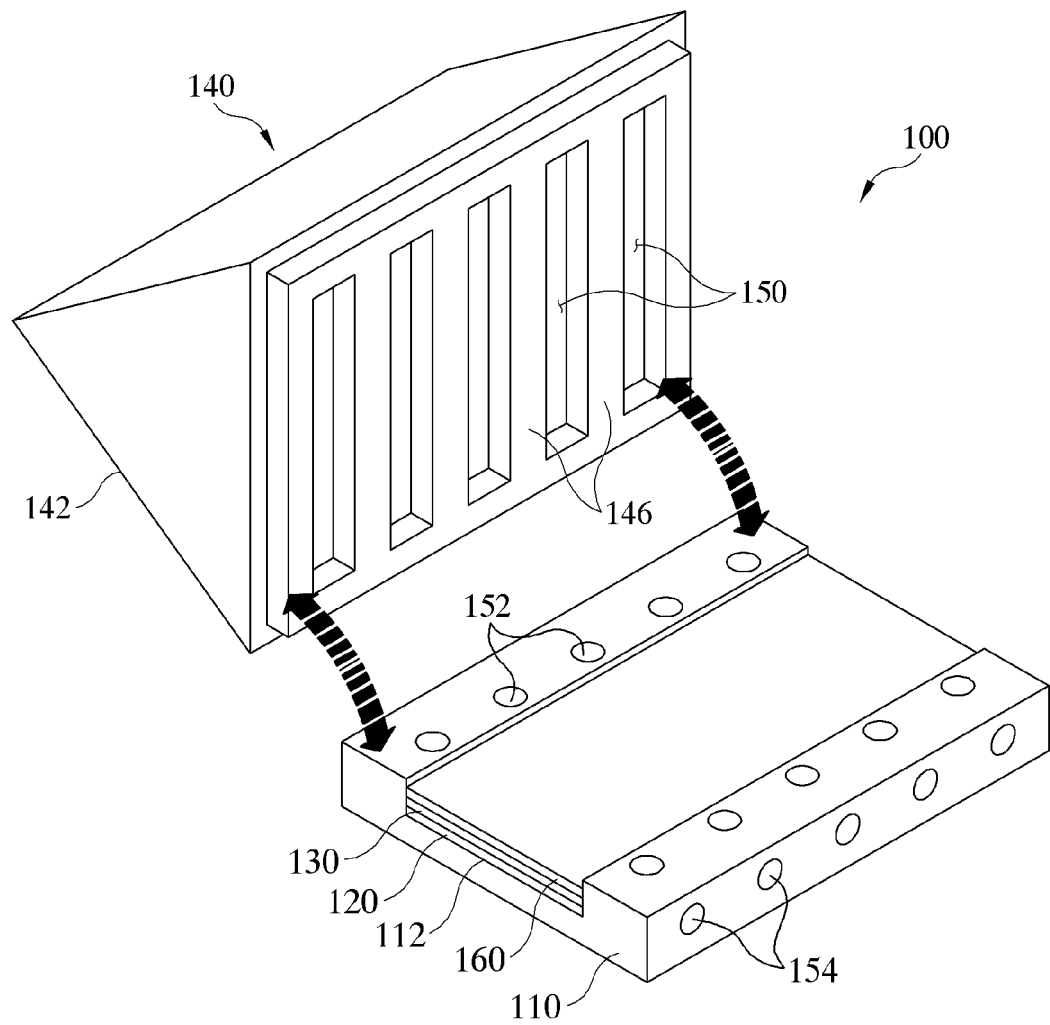
FIG. 7 is an exploded perspective view of a multi-channel type microchannel structure unit according to an example of the present invention.

FIG. 6 is a perspective view showing an example of the multi-channel type microchannel structure unit according to the present invention, and FIG. 7 is an exploded perspective view of the multi-channel type microchannel structure unit. As shown in FIG. 6 and FIG. 7, the microchannel structure unit (100) comprises a support (110), a substrate (120), an adsorption layer (160) and a cover part (140), wherein a plurality of microchannels (150) are formed to provide the multi-channel type.

As shown in FIG. 7, the support (110) is a rectangular plate, and a recess portion (112) is formed in a longitudinal direction to fit the substrate (120) and the adsorption layer (160). Inflow passages (152) and outflow passages (154) of the microchannel (150) are formed in one side and the other side of the recess portion (112), respectively. The recess portion (112), the inflow passages (152) and the outflow passages (154) are formed using a semiconductor etching technique or a light exposure technique.

The substrate (120) is provided in the recess portion of the support (110) as a rectangular plate. According to an example of the present invention, the substrate (120) is made from silicon (Si) having the complex refraction index of about 3.8391+i0.018186 at 655 nm and constant and stable physical properties with low costs. The substrate (120) may be made from semiconductor or dielectric materials other than silicon.

The adsorption layer (160) adsorbs or dissociates the low molecular weight biomaterial sample (not shown) and reflects incident light. Such surface junction part (160) is formed on a top of the substrate (120), as shown in FIG. 5 and FIG. 7.

According to an example of the present invention, the adsorption layer (160) may be at least one of a self-assembled thin film or a bio-thin film. According to another example of the present invention, a dielectric thin film (130) may be further provided between the silicon substrate (120) and the adsorption layer (160).

This dielectric thin film (130) is made using a transparent material for a thin film including a semiconductor oxide film or a glass film. A thickness of the dielectric thin film is preferably 0~1000 nm. The most common dielectric thin film (130) is for example a silicon oxide film (SiO2) that silicon is naturally oxidized and grown to a thickness of few nanometers. A refractive index of the silicon oxide film is about 1.456 at 655 nm, which helps to increase the detection sensitivity of the present invention since it exhibits a large refractive index difference from the substrate (120) made from silicon.

Also, the dielectric thin film (130) may be made of a glass film comprising optical glass. Since the dielectric thin film (130) made of silicon or a silicon oxide film or a glass film exhibits a constant refractive index relative to a metal thin film such as gold or silver, stable optical property can be provided and production costs can be lowered.

As shown in FIG. 5 to FIG. 7, the cover part (140) is provided on the support (110). It may comprise a prism (142) and a septum (146). Light entering an incident surface (143) of the prism (142) is refracted by a medium in the microchannel of the microchannel structure unit coupled to the prism (142), and the refracted light is received on the substrate at an angle which meets the P-wave anti-reflection condition.

Also, the cover part (140) comprises a number of septums (146) to form the microchannel (150) at micro-scale in a bottom of the prism (142) as shown in FIG. 7. The prism (142) and the microchannel structure may be made of a transparent material such as glass or transparent synthetic resins, and the entire structure including the septum (146) of the microchannel may be integrally formed by a method such as molding for easy manufacture.

Synthetic resins may be for example an acrylic resin such as PMMA (polymethyl methacrylate). Silicon-based materials such as silicon phosphate polymers (PDMS, polydimethylsiloxane) may be also used.

The microchannel (150) acts as a passage for introducing or discharging the buffer solution (210) containing a sample. A plurality of microchannels are formed. As previously described, each of spaces between the cover part (140) and the septums (146) is communicated with the inflow passages (152) and the outflow passages (154) formed in the support (110), and hence a plurality of the microchannels (150) are formed in the microchannel structure unit (100). A width of the microchannel (150) has micro-scale of about few millimeters or 1 mm or less.

Figure 8:
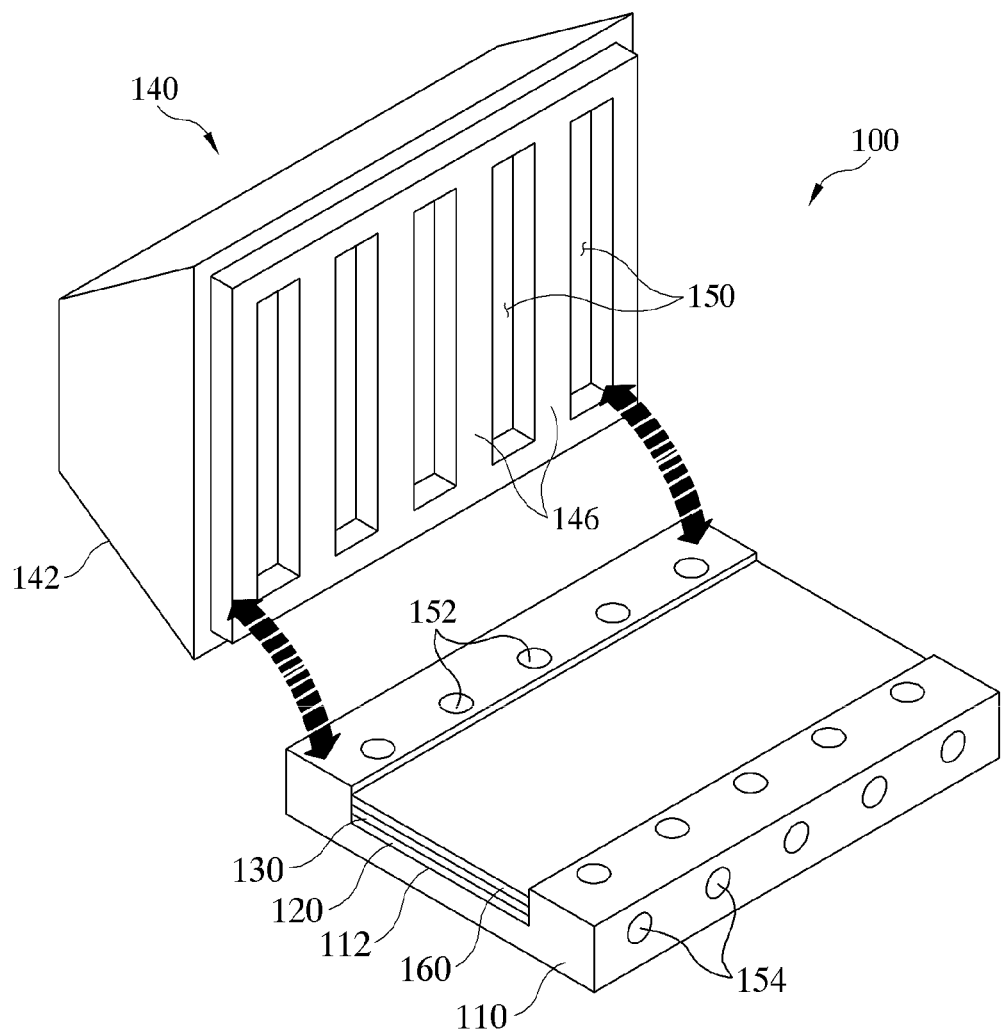
FIG. 8 is a perspective view of a multi-channel type microchannel structure unit according to another example of the present invention.

FIG. 8 is a perspective view showing another example of the multi-channel type microchannel structure unit according to the present invention. As shown in FIG. 8, the multi-channel type microchannel structure unit (100) may have a tripozoidal cross-section of the prism (142). In this case, the polarized light-generating part (300) and the polarized light-detecting part (400) as shown in FIG. 5 are securely fixed at a position such that incident light or reflected light is received on the incident surface (143) or the reflective surface (144) at the perpendicular or an angle close to the perpendicular not to significantly change the polarization of the light. A flat plate may be used for a simple and convenient structure instead of the prism structure, although the flat plate exhibits a loss of incident light.

Figure 9:
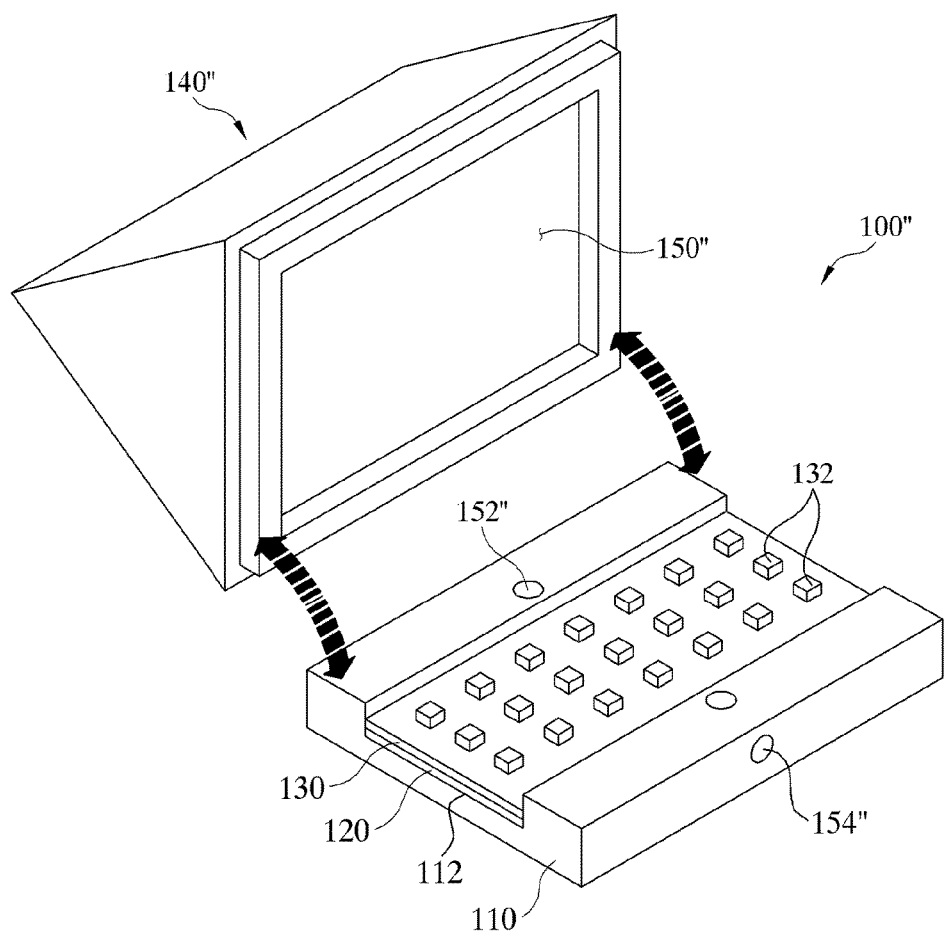
FIG. 9 is an exploded perspective view of a single-channel type microchannel structure unit according to an example of the present invention.

FIG. 9 is an exploded perspective view showing an example of the single-channel type microchannel structure unit according to the present invention. As shown in FIG. 9, the single-channel type microchannel structure unit (100) has one microchannel (150). That is, the cover part (140) has the prism (142) and a pair of septums (146) formed in both ends of the bottom of the prism, and the support (110) is provided with one inflow passage (152) and one outflow passage (154), thereby forming the microchannel (150) of a single channel.

A plurality of different self-assembled monolayers (SAM) (132) are formed onto the substrate, or different adsorption layers are formed onto identical self-assembled monolayers. The self-assembled monolayer (132) is formed by spontaneously arranging monomers made of a head group and a tail group by chemical adsorption of the molecules. The interfacial property of individual self-assembled monolayer (132) may be changed by chemically modifying a functional group in the tail group of individual self-assembled monolayer (132). That is, various adsorption and dissociation kinetics of biomaterials can be simultaneously measured since individual self-assembled monolayer (132) has a sensor mechanism showing different adsorption and dissociation for a sample.

As shown in FIG. 5, the sample injection part (200) injects the buffer solution (210) containing a low molecular weight biomaterial sample (not shown) into the inflow passage (152) of the microchannel (150). The sample injection part (200) is configured to dissolve the sample in the buffer solution (210) at a constant concentration, and has a valve device (not shown) to inject or block the injection of the buffer solution (210) into the microchannel (150).

The sample injection part (200) may inject the buffer solution (210) into each microchannel (150) at a different concentration of the sample or at a time interval. When the buffer solution (210) is injected into the microchannel (150), a portion of the sample (not shown) is adsorbed on the dielectric thin film (130) to form a desired thickness of the adsorption layer (160). The adsorption layer (160) may be a multilayer film comprising the self-assembled monolayer (132) for various junction properties of various biomaterials, an immobilization substance, and various biomaterials including low molecular weight materials bonded with the immobilization substance.

As shown in FIG. 5, the polarized light-generating part (300) irradiates incident light polarized through the incident surface (143) of the prism (142) of the microchannel structure unit (100) on the adsorption layer (160). The polarized light-generating part (300) comprises necessarily a light source (310) and a polarizer (320), and optionally comprises a collimating lens (330), a focusing lens (340) or a first compensator (350).

The polarizer (320) and the first compensator (350) may be rotatable, or may be provided with other polarization-modulating means. The polarized incident light has polarized components of p-wave and s-wave, and light close to p-wave may be received to increase a signal to noise ratio. In the present invention, the incident light should be irradiated at an angle (θ) which meets the p-wave anti-reflection condition. A complex reflection coefficient ratio (ρ) in the ellipsometric equation is represented by a ratio of p-wave reflection coefficient ratio (Rp) to s-wave reflection coefficient ratio (Rs), i.e., ρ=Rp/Rs. The p-wave anti-reflection condition means a condition that p-wave reflection coefficient ratio (Rp) has a value close to 0. The p-wave anti-reflection condition is similar to the surface plasmon resonance condition of the conventional SPR sensor, and it is a condition that the detection sensitivity of the present invention is maximized.

The light source (310) irradiates monochromatic light in a wavelength range of infrared, visible or ultraviolet rays, or white light. The light source (310) may be various lamps, light-emitting diodes (LED), lasers, laser diodes (LE) and the like. The light source (310) may have a structure capable of varying a wavelength depending on an optical system. Meanwhile, an optical signal of reflected light may have relatively smaller intensity in the vicinity of said p-wave anti-reflection condition. In this case, to enable high sensitivity measurement, light may be irradiated at a high quantity using a laser or a laser diode (LD) to increase a signal to noise ratio.

The polarizer (320) has a polarizing plate to polarize light irradiated from the light source (310). Polarized components are p-wave parallel to the incident surface and s-wave perpendicular to the incident surface.

The collimating lens (330) collects light from the light source (310) and supplies parallel lights to the polarizer (320). The focusing lens (340) converges parallel lights passing through the polarizer (320) to increase a quantity of incident light. The first compensator (350) acts to cause phase lag in polarized components of the incident light.

As shown in FIG. 5, the polarized light-detecting part (400) receives light reflected from the reflective surface (144) of the prism (142) in the adsorption layer (160) and detects a change in polarization of the reflected light. The polarized light-detecting part (400) necessarily comprises an analyzer (analyzer) (410), a light detector (detector) (420) and a processor (430), and optionally comprises a second compensator (440) and a spectrometer (450). The analyzer (410), which is a counterpart of the polarizer (320), has a polarizing plate to polarize again the reflected light, thereby controlling a polarization degree of the reflected light or an orientation of a polarizing surface. Also, depending on an optical system, the analyzer (410) may be rotatable, or may be further provided with a polarization modulating means to do phase change or elimination of polarized components and the like.

The light detector (420) detects the reflected and polarized light to obtain optical data and converts the data to an electrical signal. The optical data includes information on the change of polarization in the reflected light. The light detector (420) may be a CCD-type solid state imaging element, a photomultiplier tube (PMT) or a silicon photo diode.

The processor (430) receives the electrical signal from the light detector (420) and outputs calculated values. The processor (430) contains a desired interpretation program using reflectometry and ellipsometry. The processor (430) extracts and interprets the optical data converted to the electrical signal, in order to calculate values such as an adsorption concentration of the sample, a thickness of the adsorption layer (160), an adsorption constant, a dissociation constant, a refractive index and the like. To increase detection sensitivity, preferably the processor (430) calculates such values by computing ellipsometric constants Ψ and Δ on a phase difference in ellipsometry.

The second compensator (440) controls polarized components of the reflected light by causing phase lag. The second compensator (440) may be rotatable, or may be further provided with other polarization modulating means.

The spectrometer (450) is used when the light source (310) emits white light. In this case, it resolves the reflected light, and separates the reflected light having wavelengths in a narrow band to transfer it to the light detector (420). The light detector (420) may be a two-dimensional sensor such as a CCD-type solid state imaging element to obtain optical data on distribution of the reflected light.

[Simultaneous Measurement of the Characteristics Molecular Junctions and the Refractive Index of a Buffer Solution]

Hereinafter, a method for simultaneously measuring the characteristics of molecular junctions and the refractive index of a buffer solution and the principle thereof will be described with reference to the accompanying drawings.

Figure 10:
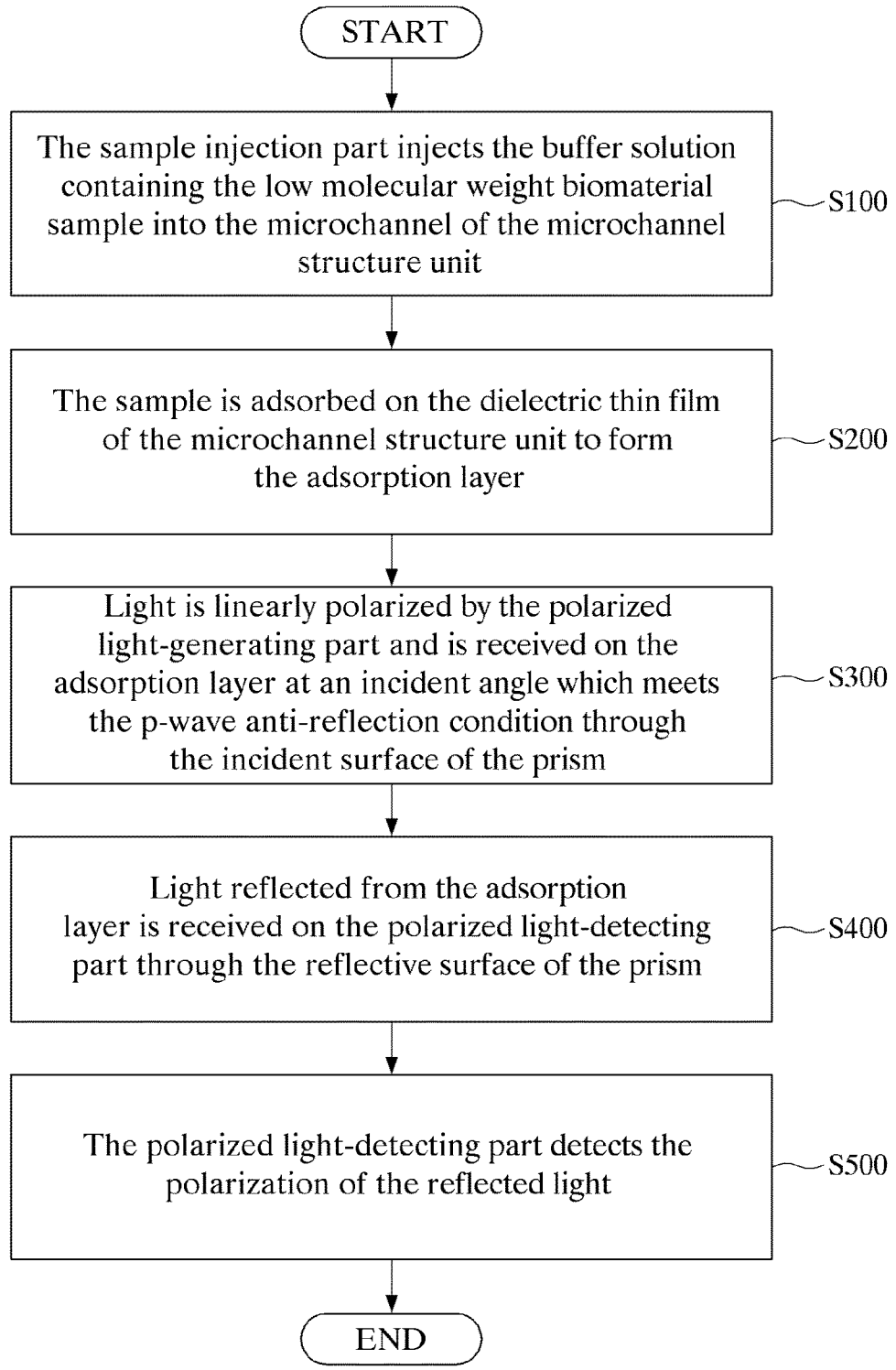
FIG. 10 is a flow chart illustrating the method for simultaneously measuring the characteristics of molecular junctions and the refractive index of a buffer solution according to an example of the present invention.

FIG. 10 is a flow chart illustrating the method for simultaneously measuring the characteristics of molecular junctions and the refractive index of a buffer solution according to the present invention. As shown in FIG. 10, the measurement method according to the present invention comprises a first step (S100) to a fifth step (S500).

As in FIG. 5, in the first step (S100), the sample injection part (200) dissolves a sample of a biomaterial including a low molecular weight material in the buffer solution (210) and injects the sample into the microchannel (150) of the microchannel structure unit (100). The sample injection part (100) may inject the buffer solution (210) containing different concentrations of the sample into each microchannel (150).

Furthermore, the buffer solution (210) may be injected into each microchannel (150) in a time interval. Also, the buffer solution (210) may be injected into some of the microchannels (150) and the other microchannels (150) may not be used.

In the second step (S200), the biomaterial sample (not shown) is adsorbed on the substrate (120) or the dielectric thin film (130) to form the adsorption layer (160).

The sample may be adsorbed on a plurality of adsorption layers onto a plurality of different self-assembled monolayers (132), or identical self-assembled monolayers are formed on the single channel type microchannel structure unit (100) as shown in FIG. 9 to form adsorption layers having different junction characteristics.

In the third step (S300), light irradiated from the light source (310) is polarized by the polarizer (320) and is received on the adsorption layer (160) through the prism (142) of the microchannel structure unit (100). After the light passes through the incident surface of the prism (142), the light is refracted at a desired angle according to the refractive index of the buffer solution (210) present in the bottom of the prism (142), followed by entering the adsorption layer (160). In this case, the polarized incident light has polarized components of p-wave and s-wave. Also, the incident light should have an incident angle (θ) which meets the p-wave anti-reflection condition.

In the fourth step (S400), light reflected from the adsorption layer (160) enters the polarized light-detecting part (400) through the prism (142) of the microchannel structure unit (100). The reflected light is an elliptically polarized state.

In the fifth step (S500), the polarized light-detecting part (400) detects the polarization of the reflected light. Specifically, firstly the elliptically polarized reflected light is received on the adsorption layer (160) by the analyzer (410) and only light for polarization is passed.

Then, the light detector (420) detects a change in polarized components of the reflected light to obtain a desired optical data, and converts the data to an electrical signal to transfer it to the processor (430).

Then, the processor (430) containing a program using reflectometry or ellipsometry extracts and interprets the optical data converted to the electrical signal to calculate values such as an adsorption concentration of the sample, an adsorption and dissociation constant, a refractive index of the sample, a refractive index of the buffer solution, and the like.

In the present invention, the processor (430) calculates an ellipsometric constant Δ on a phase difference in ellipsometry to determine the refractive index of the buffer solution, and calculates an ellipsometric constant Ψ on an amplitude ratio to determine the junction kinetics. In this way, since the ellipsometric constant Δ on a phase difference is only sensitive to the refractive index change of the buffer solution and is little affected by the junction characteristics at the P-wave anti-reflection condition, the refractive index change of the buffer solution may be only determined. The ellipsometric constant Ψ on an amplitude ratio is often changed depending on the junction characteristics of the material.

Accordingly, the junction characteristics of the sample contained in the buffer solution is determined as Ψ, and simultaneously the refractive index change of the buffer solution with the sample dissolved therein or the refractive index change of the buffer solution containing a solvent such as DMSO added for dissolving the sample is determined as Δ, thereby determining only pure junction characteristics.

Experimental Example

FIG. 11 is a graph illustrating a change of elliposmetric constants Ψ and Δ according to an incident angle at the perpendicular incident condition of the prior patent when the buffer solution (210) has different refractive indexes.

In this experiment, a wavelength of the light source (310) is 655 nm, a thickness of the bio-thin film adsorption layer including the self-assembled monolayer is 4 nm, and a refractive index (n) of the prism is 1.721 (SF10). In this case, an incident angle corresponding to the P-wave anti-reflection condition has been found to be around 70.85° where a value of the ellipsometric constant Ψ is dramatically changed.

In FIG. 11, the buffer solution (210) exhibits the refractive index of 1.3330 in the full-line graph, and the refractive index of 1.3332 in the dotted-line graph. The arched graph shows a change of the ellipsometric constant Ψ according to an amplitude ratio, and the linear graph shows a change of the ellipsometric constant Δ according to a phase difference. In FIG. 11, the ellipsometric constants Ψ and Δ exhibit a minor change according to the refractive index change of the buffer solution.

Figure 12:
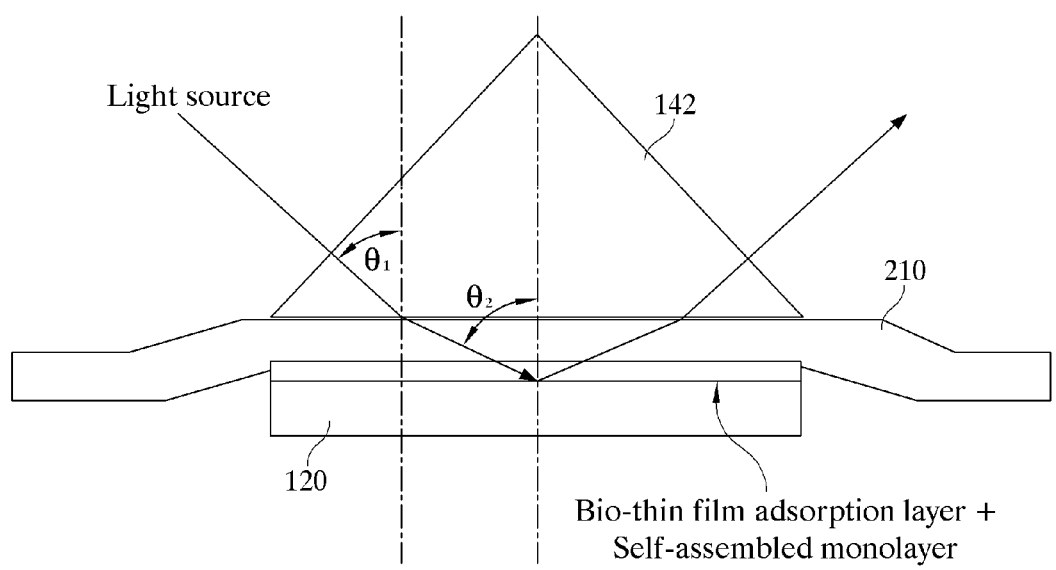
FIG. 12 is a cross-sectional view showing a light incident mechanism of a prism that light enters a boundary surface of the prism and a buffer solution at an inclined angle and is refracted by a refractive index difference between the prism and the buffer solution to enter a substrate with meeting a P-wave anti-reflection condition.
Figure 13:
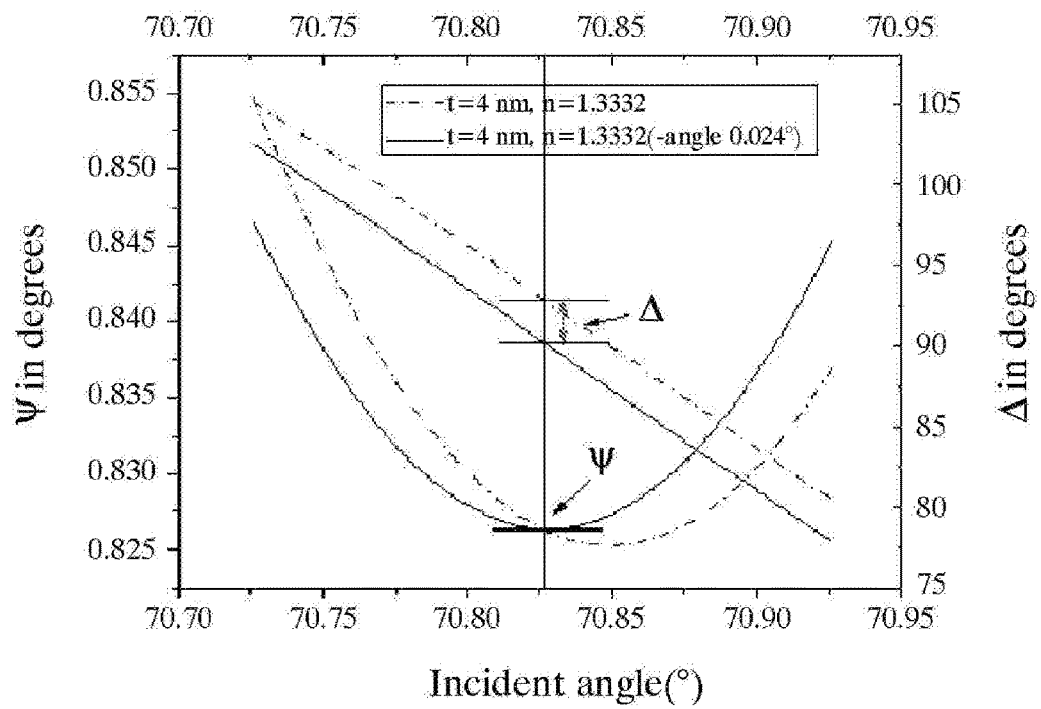
FIG. 13 is a graph illustrating a change in ellipsometric constants $\Psi$ and $\Delta$ relative to an incident angle according to the refractive index change of a buffer solution measured by using the apparatus for simultaneously measuring the characteristics of molecular junctions and the refractive index of a buffer solution according to an example of the present invention.

However, as in FIG. 12, when light is received through a prism incident mechanism, the light enters a boundary surface at an inclined angle of about θ2=70.85°. When the light is received from the prism to the buffer solution, the angle exhibits the change of about 0.024° by the refractive index change of the buffer solution (0.0002). Since the P-wave anti-reflection condition is around θ2=70.85° and the angle is changed into 70.826° by the refractive index change of the buffer solution, which is 0.024° smaller than the previous angle, Ψ and Δ graphs are made as shown in FIG. 13. Since the angle of the P-wave anti-reflection condition is little changed according to the refractive index change, Ψ and Δ values are determined at 70.826°, a 0.024° smaller angle.

In FIG. 13, when the buffer solution (210) has different refractive indexes, the buffer solution (210) exhibits the refractive index of 1.3330 in the full-line graph, and the refractive index of 1.3332 in the dotted-line graph. As shown in FIG. 13, from the results measured according to a change of an incident angle using the prism mechanism, it has been found that the Ψ value is little changed as the minor change at the perpendicular incident condition is more counteracted, while the Δ value is greatly changed. In other words, the ellipsometric constant Δ on a phase difference is sensitive to the refractive index change of the buffer solution, but is little affected by the junction property, the refractive index change of the buffer solution can be determined with high sensitivity. The ellipsometric constant Δ is greatly changed as the thin film has a smaller thickness. Accordingly, when it is used in a study to analyze a change in physical properties or junction properties of a material by measuring a refractive index change, it is possible to measure a refractive index with an ultrahigh sensitivity compared to the conventional SPR method.

Additionally, before a continuously supplied buffer solution and a buffer solution with the refractive index changed by a solvent and the like used in a sample is supplied to the sensor through the microchannel, by achieving a minimum mixing of these two solutions by a valve device, the pure junction kinetics and the refractive index change of the buffer solution can be simultaneously measured.

Additionally, since the ellipsometric constant Ψ on an amplitude ratio is changed with high sensitivity according to the junction property of a sample, the junction kinetics of the sample can be accurately measured based on a value of the ellipsometric constant Ψ on an amplitude ratio. Further, as shown in FIG. 11, it can be seen that the ellipsometric constant Ψ on an amplitude ratio is little changed according to the refractive index change of the buffer solution (1.333→1.3332) at the incident angle of 70.85°.

In particular, it can be seen that the angle is shifted at an angle about 0.024° smaller than the perpendicular incident angle at the prism incident mechanism, and a change of the Ψ value before and after the buffer solution is injected is more reduced relative to a change of the Ψ value by the refractive index change of the buffer solution at the perpendicular incident condition. This situation is caused in a positive change of the refractive index (1.333→1.3332). In most experiments for measuring the junction kinetics, a refractive index of a solvent or an additional material used for dissolving a sample is often higher than that of a pure buffer solution. In this case, by minimizing a change of the Ψ value by the refractive index change of the buffer solution before and after injection, it is possible to reduce a measurement error due to the refractive index change of the buffer solution.

What is claimed is:

1. An apparatus for simultaneously measuring the characteristics of molecular junctions and the refractive index of a buffer solution comprising:
   a microchannel structure unit provided with
      a substrate made of a support and one of a semiconductor or a dielectric material formed on the support, and
      a cover of a prism structure fitted on the support, the prism structure having a bottom including a plurality of septums forming a microchannel;
   a sample injector that injects a buffer solution containing a biomaterial sample into the microchannel to form an adsorption layer of the biomaterial sample on one of the semiconductor or dielectric material formed on the support;
   a polarized light generator that irradiates incident light polarized through an incident surface of the prism structure onto the adsorption layer at an incident angle of a P-wave anti-reflection condition; and
   a polarized light detector comprising a light detector and a polarizer that detects a change in polarization of reflected light off the adsorption layer,
   wherein the irradiated incident light being configured to exit through a first boundary surface on the bottom of the prism structure through the microchannel and onto the adsorption layer, and the reflected light off the adsorption layer through the microchannel being configured to enter through a second boundary surface of the bottom of the prism structure for detection by the polarized light detector,
   wherein the first and second boundary surfaces being substantially parallel to the adsorption layer of the biomaterial sample on one of the semiconductor or the dielectric material formed on the support.

2. The apparatus for simultaneously measuring the characteristics of molecular junctions and the refractive index of a buffer solution of claim 1, further comprising a dielectric thin film provided between the substrate and the adsorption layer, and the dielectric thin film is made from a transparent semiconductor oxide film or a glass film, and a thickness thereof is greater than 0~1000 nm.

3. An apparatus for simultaneously measuring the characteristics of molecular junctions and the refractive index of a buffer solution comprising:
   a microchannel structure unit provided with
      a substrate made of a support and one of a semiconductor or a dielectric material formed on the support,
      a cover fitted on the support, the cover including a flat plate structure having
      a bottom including a plurality of septums forming a microchannel;
   a sample injector that injects a buffer solution containing a biomaterial sample into the microchannel to form an adsorption layer of the biomaterial sample on one of the semiconductor or dielectric material formed on the support;
   a polarized light generator that irradiates incident light polarized through a first boundary surface of the bottom of the flat plate through the microchannel onto the adsorption layer at an incident angle of a P-wave anti-reflection condition; and
   a polarized light detector comprising a light detector and a polarizer that detects a change in polarization of reflected light after the reflected light enters a second boundary surface of the bottom of the flat plate from the adsorption layer, wherein the septums have a surface disposed above a top surface of the adsorption layer, and
wherein the first and second boundary surfaces being substantially parallel to the adsorption layer of the biomaterial sample on one of the semiconductor or the dielectric material formed on the support.

4. The apparatus for simultaneously measuring the characteristics of molecular junctions and the refractive index of a buffer solution of claim 1, wherein the adsorption layer is a multilayer film consisting of a self-assembled monolayer for junction characteristics of various biomaterials, an immobilization substance and a biomaterial including low molecular weight materials bonded with the immobilization substance.

5. The apparatus for simultaneously measuring the characteristics of molecular junctions and the refractive index of a buffer solution of claim 1, wherein the polarized light generator comprises a light source configured to irradiate a desired light and a polarizer configured to polarize the irradiated desired light.

6. The apparatus for simultaneously measuring the characteristics of molecular junctions and the refractive index of a buffer solution of claim 5, wherein the light source irradiates one of monochromatic light or white light.

7. The apparatus for simultaneously measuring the characteristics of molecular junctions and the refractive index of a buffer solution of claim 5, wherein the light source is one of a laser or a laser diode.

8. The apparatus for simultaneously measuring the characteristics of molecular junctions and the refractive index of a buffer solution of claim 5, wherein the light source is one of a laser or a laser diode which has a variable form of wavelength.

9. The apparatus for simultaneously measuring the characteristics of molecular junctions and the refractive index of a buffer solution of claim 5, wherein the polarized light generator comprises:
at least one of a collimating lens to provide parallel lights to the polarizer;
a focusing lens to converge the parallel lights passing through the polarizer to increase the quantity of incident light; and
a first compensator to cause phase lag in polarized components of the incident light.

10. The apparatus for simultaneously measuring the characteristics of molecular junctions and the refractive index of a buffer solution of claim 9, wherein the polarizer and the first compensator are one of rotatable or have an additional polarization modulator.

11. A system for simultaneously analyzing the characteristics of molecular junctions and the refractive index of a buffer solution comprising:
a microchannel structure unit provided with
a substrate made of a support and one of a semiconductor or a dielectric material formed on the support,
a cover fitted on the support, the cover including a prism structure having a bottom including a plurality of septums forming a microchannel;
a sample injector that injects a buffer solution containing a biomaterial sample into the microchannel to form an adsorption layer of the biomaterial sample on the one of a semiconductor or a dielectric material formed on the support;
a polarized light generator that irradiates incident light polarized through a first boundary surface of the bottom of the prism structure through the microchannel onto the adsorption layer at an incident angle of a P-wave anti-reflection condition;
a polarized light detector comprising a light detector and a polarizer that detects a change in polarization of reflected light when the reflected light through the microchannel enters a second boundary surface of the bottom of the prism structure from the adsorption layer; and
an analyzer electrically connected to the polarized light detector for analyzing the refractive index of the buffer solution and the characteristics of molecular junctions of the biomaterial sample based on the polarization change,
wherein the septums have a surface disposed above a top surface of the adsorption layer, and
wherein the first and second boundary surfaces being substantially parallel to the adsorption layer of the biomaterial sample on one of the semiconductor or the dielectric material formed on the support.

12. The system for simultaneously analyzing the characteristics of molecular junctions and the refractive index of a buffer solution of claim 11, wherein the polarized light detector comprises an analyzer configured to polarize reflected light wherein the light detector detects the polarized reflected light to obtain optical data.

13. The system for simultaneously analyzing the characteristics of molecular junctions and the refractive index of a buffer solution of claim 12, wherein the light detector is any one of a CCD type solid state imaging element, a photomultiplier tube and a silicon photodiode.

14. The system for simultaneously analyzing the characteristics of molecular junctions and the refractive index of a buffer solution of claim 12, wherein the analyzer comprises a processor which is electrically connected to the light detector to calculate values based on the optical data, and
wherein the processor calculates an ellipsometric constant on a phase difference in ellipsometry to determine the refractive index of the buffer solution, and calculates an ellipsometric constant on an amplitude ratio to determine values including an adsorption concentration of the biomaterial sample, an adsorption and dissociation constant of the biomaterial sample.

15. The system for simultaneously analyzing the characteristics of molecular junctions and the refractive index of a buffer solution of claim 11, wherein the polarized light detector further comprises at least one of a second compensator to cause phase lag in polarized components of the reflected light and a spectrometer to resolve the reflected light.

16. The system for simultaneously analyzing the characteristics of molecular junctions and the refractive index of a buffer solution of claim 15, wherein the analyzer and the second compensator are rotatable, or have an additional polarization modulator.

17. A method for simultaneously measuring the characteristics of molecular junctions and the refractive index of a buffer solution comprising:
providing a microchannel structure unit provided with
a substrate made of a support and one of a semiconductor or a dielectric material formed on the support, and
a cover of a prism structure fitted on the support, the cover including a bottom including a plurality of septums forming a microchannel;
providing a sample injector;
providing a polarized light generator; and providing a polarized light detector comprising a light detector and a polarizer, injecting, by the sample injector, the buffer solution containing a biomaterial sample into the microchannel of the microchannel structure unit;

forming an adsorption layer by adsorbing the biomaterial sample on one of the semiconductor or dielectric material formed on the support, wherein the plurality of septums have a surface disposed above a top surface of the adsorption layer;

polarizing, by the polarized light generator, a desired light by the polarized light generator and irradiating the desired light through an incident surface of a bottom of the prism structure, the incident surface being parallel with the adsorption layer;

receiving the irradiated incident light through the microchannel on the adsorption layer at an incident angle which meets the P-wave anti-reflection condition through the incident surface of the bottom of the prism structure of the microchannel structure unit;

receiving the irradiated incident light reflected from the adsorption layer through the microchannel on the polarized light detector at an incident angle which meets the P-wave anti-reflection condition through an incident window on the bottom of the prism, the incident window being parallel with the adsorption layer; and detecting, at the polarized light detector, the polarization of the reflected light using ellipsometry or reflectometry.

18. The method for simultaneously measuring the characteristics of molecular junctions and the refractive index of a buffer solution of claim 17, wherein the detecting of the polarization of the reflected light further comprises:

polarizing the reflected light by an analyzer;

detecting the polarized reflected light by the light detector to obtain a desired optical data;

calculating an ellipsometric constant on a phase difference in ellipsometry by the analyzing means based on the optical data to determine the refractive index of the buffer solution; and calculating an ellipsometric constant on an amplitude ratio to determine values including an adsorption concentration of the sample, an adsorption and dissociation constant of the sample.

* * * * *